(12) United States Patent
Payne et al.

(10) Patent No.: US 9,316,634 B2
(45) Date of Patent: Apr. 19, 2016

(54) INDUCIBLE CELL-BASED MODEL FOR THE STUDY OF FRIEDREICH'S ATAXIA

(71) Applicant: Indiana University Research & Technology Corporation, Indianapolis, IN (US)

(72) Inventors: Ronald Mark Payne, Zionsville, IN (US); Clifford M. Babbey, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/276,348

(22) Filed: May 13, 2014

(65) Prior Publication Data

US 2014/0335516 A1    Nov. 13, 2014

Related U.S. Application Data

(60) Provisional application No. 61/822,615, filed on May 13, 2013.

(51) Int. Cl.
  *G01N 33/50* (2006.01)
  *C12N 15/113* (2010.01)

(52) U.S. Cl.
  CPC .......... *G01N 33/5061* (2013.01); *C12N 15/113* (2013.01); *C12N 2310/531* (2013.01); *G01N 2800/28* (2013.01)

(58) Field of Classification Search
  None
  See application file for complete search history.

(56) References Cited

PUBLICATIONS

Taxman et al. Chapter 10: Short Hairpin RNA (shRNA): Design, Delivery, and Assessment of Gene Knockdown. in Methods in Molecular Biology, vol. 629, pp. 139-156, 2010.*

Fuerst et al. Transfer of the inducible lac repressor/operator system from *Escherichia coli* to a vaccinia virus expression vector. Proceedings of the National Academy of Sciences, USA, vol. 86, pp. 2549-2553, Apr. 1989.*

Jiralerspong et al. Frataxin shows developmentally regulated tissue-specific expression in the mouse embryo. Neurobiology of Disease, vol. 4, pp. 103-113, 1997.*

EST Profile for Mm.7319—Fxn: Frataxin. Printed from http://www.ncbi.nlm.nih.gov/UniGene/ESTProfileViewer.cgi?uglist=Mm.7319 on Apr. 1, 2015 as pp. 1/3-3/3.*

Wagner et al., "Widespread and Enzyme-independent Nε-Acetylation and N•-Succinylation of Proteins in the Chemical Conditions of the Mitochondrial Matrix*♦," The Journal of Biological Chemistry, vol. 288, No. 40, pp. 29036-29045, Oct. 4, 2013.

Wagner, et al., Friedreich's ataxia reveals a mechanism for coordinate regulation of oxidative metabolism via feedback inhibition of the SIRT3 deacetylase, Human Molecular Genetics, 2012, vol. 21, No. 12, pp. 2688-2697.

Vyas et al., A TAT-Frataxin fusion protein increases lifespan and cardiac function in a conditional Friedreich's ataxia mouse model, Human Molecular Genetics, 2012, vol. 21, No. 6, pp. 1230-1247.

Cinato E, Mirotsou M, Sablitzky F (2001) Cre-mediated transgene activation in the developing and adult mouse brain. Genesis 31:118-125.

Lu C, Cortopassi G (2007) Frataxin knockdown causes loss of cytoplasmic iron—sulfur cluster functions, redox alterations and induction of heme transcripts. Archives of biochemistry and biophysics 457:111-122.

Napoli E, Morin D, Bernhardt R, Buckpitt A, Cortopassi G (2007) Hemin rescues adrenodoxin, heme a and cytochrome oxidase activity in frataxin-deficient oligodendroglioma cells. Biochimica et Biophysica Acta 1772:773-780.

Santos MM, Ohshima K, Pandolfo M (2001) Frataxin deficiency enhances apoptosis in cells differentiating into neuroectoderm. Human Molecular Genetics 10:1935-1944.

Schoenfeld RA, Napoli E, Wong A, Zhan S, Reutenauer L, Morin D, Buckpitt AR, Taroni F, Lonnerdal B, Ristow M, Puccio H, Cortopassi GA (2005) Frataxin deficiency alters heme pathway transcripts and decreases mitochondrial heme metabolites in mammalian cells. Human Molecular Genetics 14:3787-3799.

Stehling O, Elsasser HP, Bruckel B, Muhlenhoff U, Lill R (2004) Iron—sulfur protein maturation in human cells: evidence for a function of frataxin. Human Molecular Genetics 13:3007-3015.

Tan G, Napoli E, Taroni F, Cortopassi G (2003) Decreased expression of genes involved in sulfur amino acid metabolism in frataxin-deficient cells. Hum.Mol.Genet. 12:1699.

Zanella I, Derosas M, Corrado M, Cocco E, Cavadini P, Biasiotto G, Poli M, Verardi R, Arosio P (2008) The effects of frataxin silencing in HeLa cells are rescued by the expression of human mitochondrial ferritin. Biochimica et Biophysica Acta 1782:90-98.

* cited by examiner

*Primary Examiner* — Jennifer Dunston
(74) *Attorney, Agent, or Firm* — Stinson Leonard Street LLP

(57) ABSTRACT

Isolated transduced cells exhibiting FRDA characteristics in an inducible fashion are disclosed. Isolated transduced cells comprise an expression vector having a nucleic acid sequence encoding an shRNA for frataxin protein knockdown and a heterologous expression control sequence. Additionally, methods of screening for a candidate therapeutic agent for treating Friedreich's Ataxia using isolated transduced cells are disclosed. Further, a recombinant nucleic acid construct for frataxin knockdown is disclosed that comprises a nucleic acid encoding an shRNA operably linked to a heterologous expression control sequence and expressing an shRNA molecule in a dose-responsive fashion.

18 Claims, 4 Drawing Sheets

SEQUENCE LISTING

<160> NUMBER OF SEQ ID NOS: 3

<210> SEQ ID NO 1
<211> LENGTH: 21

```
<212> TYPE: DNA
<213> ORGANISM: Artificial Sequence
<220> FEATURE:
<223> OTHER INFORMATION: Synthetic

<400> SEQUENCE: 1
gacttgtctt cattggccta t                                        21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
gagttctttg aagacctcgc a                                        21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
cctccagatt ctgaacatca a                                        21
```

INDUCIBLE CELL-BASED MODEL FOR THE STUDY OF FRIEDREICH'S ATAXIA

CROSS REFERENCE TO RELATED APPLICATIONS

This application claims priority to U.S. Provisional Patent Application No. 61/822,615 filed on May 13, 2013, which is hereby expressly incorporated by reference in its entirety.

INCORPORATION OF SEQUENCE LISTING

A paper copy of the Sequence Listing and a computer readable form of the sequence listing provided herein, containing the file named "IURTC13199_ST25.txt", which is 903 bytes in size (as measured in MICROSOFT WINDOWS® EXPLORER), and are herein incorporated by reference. This Sequence Listing consists of SEQ ID NOs: 1-3.

BACKGROUND

The present disclosure is generally related to screening methods for therapeutic agents for Friedreich's Ataxia. More particularly, the present disclosure relates to a cell-based model exhibiting metabolic characteristics of Friedreich's Ataxia and methods of screening therapeutic agents for treating Friedreich's Ataxia.

Friedreich's Ataxia (FRDA) is an autosomal recessive mitochondrial disorder caused by a homozygous triplet nucleotide repeat expansion in intron 1 of the FXN gene located on chromosome 9q21.11. This intronic expansion causes impaired transcription of the FXN gene and, consequently, a pathological deficiency of the FXN gene product frataxin. Frataxin is targeted to the mitochondrial matrix, where it is known to act as an iron-binding protein and participates in the proper assembly and function of iron-sulfur cluster (ISC) dependent proteins including complexes I, II, and III of the respiratory chain and aconitase of the tricarboxylic acid (TCA) cycle. Thus, frataxin deficiency severely compromises both cellular respiration and overall mitochondrial function leading to energetic stress and adenosine triphosphate (ATP) deficiency. Although patients develop multi-system diseases including early spinocerebellar degeneration, ataxia, and diabetes, the primary cause of death is heart failure for nearly 85% of those afflicted. Similarly, although the phenotypes of the neuron-specific enolase (NSE) and muscle creatine kinase (MCK)—Cre conditional mouse models of FRDA differ, both models develop a fatal cardiomyopathy and impaired activity of iron-sulfur cluster-dependent respiratory complexes consistent with the human disease.

Frataxin protein levels have a narrow range of efficacy for study. Heterozygote conditions for the disease have no phenotype in animals or cells in culture, and heterozygous patients have no FRDA disease. This indicates that cells are able to function in a non-disease fashion across a wide range of frataxin concentrations. However, when frataxin levels are reduced too greatly, the cells die rapidly.

Accordingly, there is a critical unmet need for novel materials and methods for studying the FRDA disease phenotype and screening for therapeutic development.

BRIEF DESCRIPTION

The present disclosure is generally related to screening methods for therapeutic agents for Friedreich's Ataxia. More particularly, the present disclosure relates to a cell-based model exhibiting metabolic characteristics of Friedreich's Ataxia and methods of screening therapeutic agents for treating Friedreich's Ataxia.

In one aspect, the present disclosure is directed to an isolated transduced cell comprising an expression vector comprising a nucleic acid sequence encoding an shRNA selected from the group consisting of SEQ ID NO: 1, SEQ ID NO: 2 and SEQ ID NO: 3, and a heterologous expression control sequence.

In another aspect, the present disclosure is directed to an isolated transduced C2C12 myoblast cell comprising a letiviral expression vector comprising a nucleic acid sequence encoding an shRNA selected from the group consisting of SEQ ID NO: 1, SEQ ID NO: 2 and SEQ ID NO: 3, and a heterologous expression control sequence, wherein the heterologous expression control sequence is an isopropylthio-β-galactoside-inducible promoter.

In another aspect, the present disclosure is directed to a method of screening for a candidate therapeutic agent for treating Friedreich's Ataxia. The method comprises culturing an isolated transduced cell comprising an expression vector comprising a nucleic acid sequence encoding an shRNA selected from the group consisting of SEQ ID NO: 1, SEQ ID NO: 2 and SEQ ID NO: 3, and a heterologous expression control sequence; inducing the isolated transduced cell to express the shRNA, wherein the shRNA reduces frataxin mRNA transcripts; contacting the isolated transduced cell with a candidate therapeutic agent; and analyzing the isolated transduced cell contacted with the candidate therapeutic agent.

In another aspect, the present disclosure is directed to a recombinant nucleic acid construct for frataxin knockdown comprising a nucleic acid encoding an shRNA selected from the group consisting of SEQ ID NO: 1, SEQ ID NO: 2 and SEQ ID NO: 3, wherein the shRNA is operably linked to a heterologous expression control sequence.

In another aspect, the present disclosure is directed to a recombinant nucleic acid construct for frataxin knockdown comprising a letiviral expression vector comprising a nucleic acid sequence encoding an shRNA selected from the group consisting of SEQ ID NO: 1, SEQ ID NO: 2 and SEQ ID NO: 3, and a heterologous expression control sequence, wherein the heterologous expression control sequence is an isopropylthio-β-galactoside-inducible promoter.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1:
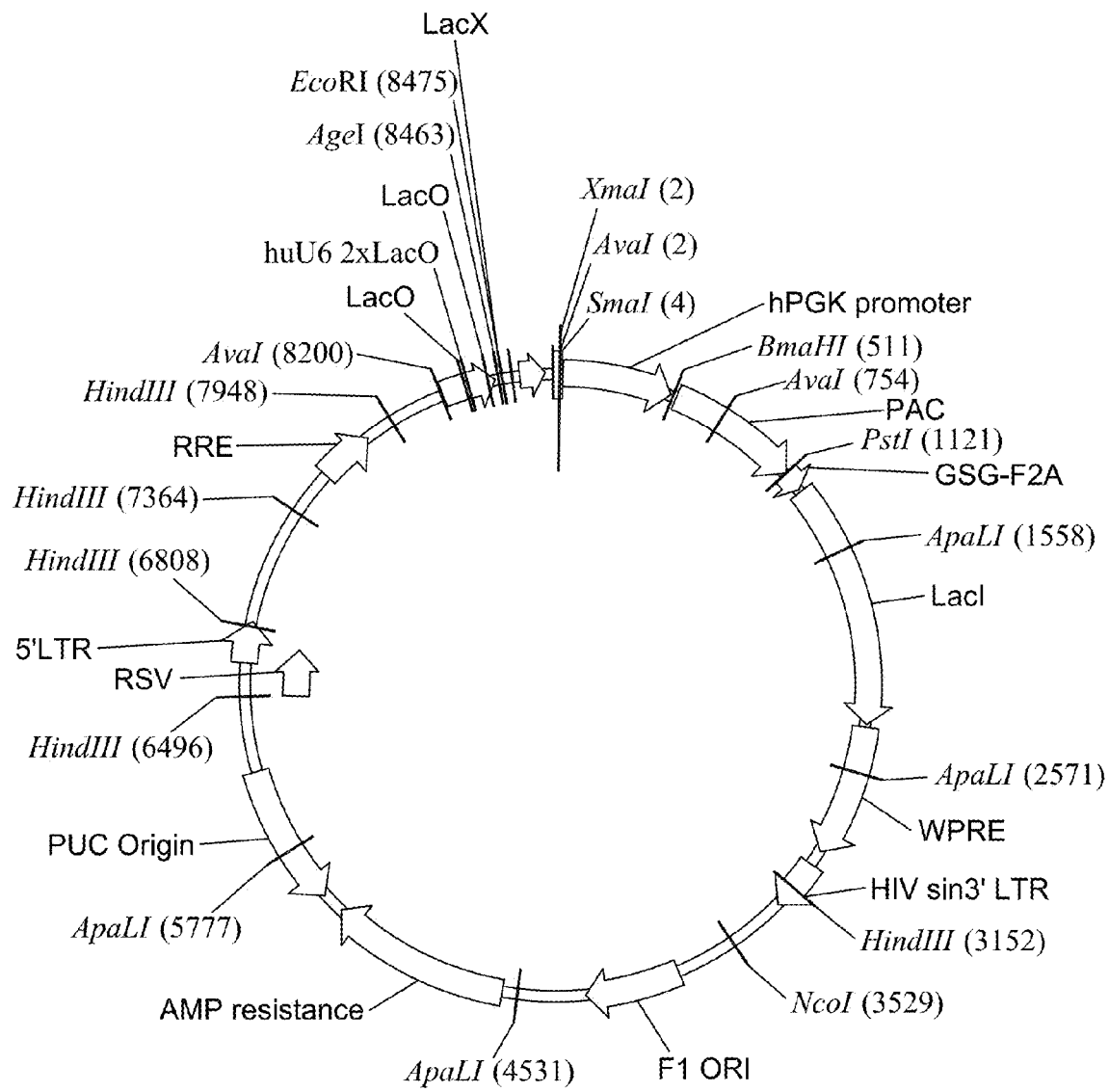
FIG. 1 depicts the pLKO-puro-IPTG-3xLacO vector map of the present disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, a cell-based model exhibiting metabolic characteristics of Friedreich's Ataxia and methods of screening therapeutic agents for treating Friedreich's Ataxia have been discovered. The shRNA used in these cells targets the frataxin gene mRNA transcript and leads to its precise, selective degradation. This results in the reduction of frataxin protein levels in the cell as a whole. In biochemical assays, this reduction or loss of frataxin protein has yielded a phenotype mimicking FRDA in animal models and humans. Because these assays are designed for medium to high-throughput, this cell line can allow for therapeutics to be tested for efficacy in an inexpensive, standard pharmacological approach.

As used herein, "heterologous" refers to sequences that are not naturally contiguous. For example, a heterologous expression control sequence such as, for example, an inducible promoter sequence, and a nucleic acid sequence encoding an shRNA selected from SEQ ID NOs: 1-3 are heterologous because the two sequences are not naturally contiguous.

The term "construct", as used herein, refers to any recombinant polynucleotide molecule. Examples of constructs may be a plasmid, a cosmid, a virus, an autonomously replicating polynucleotide molecule, a phage, or a linear or circular single-stranded or double-stranded DNA or RNA polynucleotide molecule, derived from any source, capable of genomic integration or autonomous replication, comprising a polynucleotide molecule where one or more polynucleotide molecule(s) has been linked in a functionally operative manner, i.e., operably linked.

The phrase "operably linked", as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. Nucleic acid sequences that can be operably linked may be, for example, sequences that provide gene expression functions (e.g., gene expression elements such as promoters, 5' untranslated regions, introns, protein coding regions, 3' untranslated regions, polyadenylation sites, and/or transcriptional terminators), sequences that provide DNA transfer and/or integration functions, sequences that provide for selective functions (e.g., antibiotic resistance markers, biosynthetic genes), sequences that provide scoreable marker functions (e.g., reporter genes), sequences that facilitate in vitro or in vivo manipulations of the sequences (e.g., polylinker sequences, site specific recombination sequences) and sequences that provide replication functions.

The phrase "DNA construct", as used herein refers to any DNA molecule in which two or more ordinarily distinct DNA sequences have been covalently linked. Examples of DNA constructs may be, for example, plasmids, cosmids, viruses, BACs (bacterial artificial chromosome), YACs (yeast artificial chromosome), plant minichromosomes, autonomously replicating sequences, phage, or linear or circular single-stranded or double-stranded DNA sequences, derived from any source, that are capable of genomic integration or autonomous replication. DNA constructs may be assembled by a variety of methods such as, for example, recombinant DNA techniques, DNA synthesis techniques, PCR (Polymerase Chain Reaction) techniques, or any combination of techniques.

The phrase "heterologous promoter", as used herein, refers to a promoter that is not operably linked to the nucleic acid sequence encoding an shRNA described herein in nature.

The term "expression control sequence", as used herein, refers to a nucleic acid sequence that regulates the expression of a nucleic acid sequence to which it is operatively linked. Expression control sequences are sequences that control the transcription, post-transcriptional events and translation of nucleic acid sequences.

The term "transduced", as used herein, refers to a process of introducing a nucleic acid sequence into a cell or organism. "Stable transduction" refers to a transduced nucleic acid that is incorporated into a chromosome or is capable of autonomous replication.

The term "vector", as used herein, refers to any recombinant polynucleotide construct that may be used to introduce heterologous DNA into a host cell.

Transduced Cells

In one aspect, the present disclosure is directed to an isolated transduced cell comprising an expression vector comprising a nucleic acid sequence encoding an shRNA selected from the group consisting of SEQ ID NO: 1 (GACTTGTCT-TCATTGGCCTAT), SEQ ID NO: 2 (GAGTTCTTTGAA-GACCTCGCA) and SEQ ID NO: 3 (CCTCCAGATTCT-GAACATCAA), and a heterologous expression control sequence.

A particularly suitable expression vector includes a lentiviral construct.

The isolated transduced cell can be a C2C12 myoblast cell.

Suitable heterologous expression control sequences include an inducible promoter and a constitutive promoter. A particularly suitable inducible promoter is an isopropylthio-β-galactoside-inducible promoter.

The expression vector expresses an shRNA molecule encoded by SEQ ID NO: 1 (GACTTGTCTTCATTGGC-CTAT), SEQ ID NO: 2 (GAGTTCTTTGAAGACCTCGCA) and SEQ ID NO: 3 (CCTCCAGATTCTGAACATCAA) in an inducible, dose-responsive fashion in response to IPTG stimulation. Expression of the shRNA of SEQ ID NO: 1 (GACTTGTCTTCATTGGCCTAT), SEQ ID NO: 2 (GAGT-TCTTTGAAGACCTCGCA) and SEQ ID NO: 3 (CCTCCA-GATTCTGAACATCAA) targets mRNA transcripts of the frataxin gene and precisely and selectively degrades the frataxin mRNA transcripts. Degradation of the frataxin mRNA transcripts results in the reduction of frataxin protein levels in the cell as a whole to provide a phenotype mimicking FRDA in animal models and humans.

In one particularly suitable embodiment, the present disclosure is directed to an isolated transduced C2C12 myoblast cell including a letiviral expression vector comprising a nucleic acid sequence encoding an shRNA selected from the group consisting of SEQ ID NO: 1 (GACTTGTCTTCATTG-GCCTAT), SEQ ID NO: 2 (GAGTTCTTTGAAGAC-CTCGCA) and SEQ ID NO: 3 (CCTCCAGATTCTGAA-CATCAA) and a heterologous expression control sequence, wherein the heterologous expression control sequence is an isopropylthio-β-galactoside-inducible promoter.

Methods for Screening

In another aspect, the present disclosure is directed to a method of screening for a candidate therapeutic agent for treating Friedreich's Ataxia. The method comprises culturing an isolated transduced cell comprising an expression vector comprising a nucleic acid sequence encoding an shRNA selected from the group consisting of SEQ ID NO: 1 (GACTTGTCTTCATTGGCCTAT), SEQ ID NO: (GAGTTCTTTGAAGACCTCGCA) and SEQ ID NO: 3 (CCTCCAGATTCTGAACATCAA), and a heterologous expression control sequence; inducing the isolated transduced cell to express the shRNA, wherein the shRNA reduces frataxin mRNA transcripts; contacting the isolated transduced cell with a candidate therapeutic agent; and analyzing the isolated transduced cell contacted with the candidate therapeutic agent.

The isolated transduced cell can be a C2C12 myoblast cell.

Suitable heterologous expression control sequences can be selected from an inducible promoter and a constitutive promoter. A particularly suitable inducible promoter is an isopropylthio-β-galactoside-inducible promoter.

Inducing the isolated transduced cell to express the shRNA includes contacting the isolated transduced cell with from 0 µM isopropylthio-β-galactoside (IPTG) to about 1 µM isopropylthio-β-galactoside (IPTG).

Analyzing the isolated transduced cell contacted with the candidate therapeutic agent can be, for example, by analyzing frataxin protein level, analyzing aconitase activity, analyzing protein acetylation and combinations thereof.

Frataxin protein level can be analyzed using methods known by those skilled in the art. Suitable methods can be, for example, Western blot analysis, enzyme-linked immunosorbent assay (ELISA), immunoprecipitation, immunofluorescense, mass spectrometry, Northern blot analysis to detect frataxin mRNA, quantitative RNA analysis, and analysis of mitochondrial enzymes containing an iron-sulfur cluster that depends on frataxin for activity such as, for example, complexes I, II, and III of the respiratory chain and aconitase of the tricarboxylic acid (TCA) cycle. To analyze frataxin protein level, an isolated transduced cell is induced such that the cell expresses the shRNA, and is then contacted with the candidate therapeutic agent. The frataxin protein level of the cell is analyzed using methods known by those skilled in the art and compared to the frataxin protein level of an isolated transduced cell that is induced such that the cell expresses the shRNA, but which is not contacted with the candidate therapeutic agent. A candidate therapeutic agent is identified if frataxin protein level increases or improves as compared to the frataxin protein level of the isolated transduced cell that is induced such that the cell expresses the shRNA, but which is not contacted with the candidate therapeutic agent.

Aconitase activity can be analyzed using methods known by those skilled in the art. Kits (e.g., Cayman Chemicals, Ann Arbor, Mich.) are commercially available for analyzing aconitase activity. Aconitase activity can be analyzed using a colorimetric assay to measure aconitase activity in biological samples. In the colorimetric assay, citrate is converted by aconitase into isocitrate. Isocitrate is then converted to α-ketoglutarate by Isocitrate Dehydrogenase, which produces NADPH+H from NADP. This results in a product that can convert a nearly colorless probe into an intensely colored form with a $\lambda_{max}$ at 450 nm. Aconitase is an enzyme whose functionality is directly enabled by frataxin and is a sensitive marker of the loss of frataxin protein. In one embodiment, the aconitase activity is increased in response to contacting the isolated transduced cell with the candidate therapeutic agent. To analyze aconitase activity, an isolated transduced cell is induced such that the cell expresses the shRNA, and is then contacted with the candidate therapeutic agent. The aconitase activity of the cell is analyzed using methods known by those skilled in the art and compared to the aconitase activity of an isolated transduced cell that is induced such that the cell expresses the shRNA, but which is not contacted with the candidate therapeutic agent. A candidate therapeutic agent is identified when the candidate therapeutic agent increases or improves aconitase activity in the induced transduced cell that is contacted with the candidate therapeutic agent as compared to the aconitase activity of the isolated transduced cell that is induced such that the cell expresses the shRNA, but which is not contacted with the candidate therapeutic agent.

Protein acetylation can be analyzed using methods known by those skilled in the art. Suitable methods can be, for example, Western blot analysis, enzyme-linked immunosorbent assay (ELISA), immunoprecipitation immunofluorescence, and mass spectrometry. To analyze protein acetylation, an isolated transduced cell is induced such that the cell expresses the shRNA, and is then contacted with the candidate therapeutic agent. The protein acetylation of the cell is analyzed using methods known by those skilled in the art and compared to the protein acetylation of an isolated transduced cell that is induced such that the cell expresses the shRNA, but which is not contacted with the candidate therapeutic agent. A candidate therapeutic agent is identified if protein acetylation increases or improves as compared to the protein acetylation of the isolated transduced cell that is induced such that the cell expresses the shRNA, but which is not contacted with the candidate therapeutic agent.

The candidate therapeutic agent can be a low molecular weight therapeutic agent such as, for example, small molecule drugs, and biologics such as, for example, peptides, lipids, protein drugs, protein conjugate drugs, enzymes, oligonucleotides, ribozymes and genetic material.

Expression Vector Constructs

In another aspect, the present disclosure is directed to a recombinant nucleic acid construct for frataxin knockdown including a nucleic acid encoding an shRNA selected from the group consisting of SEQ ID NO: 1 (GACTTGTCTTCATTGGCCTAT), SEQ ID NO: 2 (GAGTTCTTTGAAGACCTCGCA) and SEQ ID NO: 3 (CCTCCAGATTCTGAACATCAA), wherein the shRNA is operably linked to a heterologous expression control sequence.

A particularly suitable expression vector includes a lentiviral construct.

The shRNA molecule is selected from SEQ ID NO: 1 (GACTTGTCTTCATTGGCCTAT), SEQ ID NO: 2 (GAGTTCTTTGAAGACCTCGCA) and SEQ ID NO: 3 (CCTCCAGATTCTGAACATCAA). The expression vector expresses an shRNA molecule encoded by SEQ ID NO: 1 (GACTTGTCTTCATTGGCCTAT), SEQ ID NO: 2 (GAGTTCTTTGAAGACCTCGCA) and SEQ ID NO: 3 (CCTCCAGATTCTGAACATCAA) in an inducible, dose-responsive fashion in response to IPTG stimulation.

Suitable heterologous expression control sequences can be selected from an inducible promoter and a constitutive promoter. A particularly suitable inducible promoter is an isopropylthio-β-galactoside-inducible promoter.

In one particularly suitable embodiment, the present disclosure is directed to a recombinant nucleic acid construct for frataxin knockdown including a letiviral expression vector comprising a nucleic acid sequence encoding an shRNA selected from the group consisting of SEQ ID NO: 1 (GACTTGTCTTCATTGGCCTAT), SEQ ID NO: 2 (GAGTTCTTTGAAGACCTCGCA) and SEQ ID NO: 3 (CCTCCAGATTCTGAACATCAA), and a heterologous expression control sequence, wherein the heterologous expression control sequence is an isopropylthio-β-galactoside-inducible promoter.

EXAMPLES

Example 1

In this Example, the production of the shRNA FXN expression vector is described.

The inducible expression vector for the knockdown of frataxin mRNA was designed by analyzing the frataxin mRNA sequence. SEQ ID NO: 1 (GACTTGTCTTCATTGGCCTAT), SEQ ID NO: 2 (GAGTTCTTTGAAGACCTCGCA) and SEQ ID NO: 3 (CCTCCAGATTCTGAACATCAA) were identified as possible target sequences for shRNA knockdown and custom cloned as lentivirus particles (Sigma Aldrich, St. Louis, Mo.). The three sequences were custom cloned into the pLKO-puro-IPTG-3xLacO vector, which expresses the shRNA product under the control of a Lac operator mechanism and was modified in a manner that made it inducible, in a dose-responsive fashion, using IPTG (see, FIG. 1).

Example 2

In this Example, the development of the inducible cell line is described.

Mouse C2C12 myoblast cells were stably transduced with the letiviral construct described in Example 1. The expressed shRNA targeted the frataxin gene mRNA transcript in the cells and lead to its precise, selective degradation. Degradation of the mRNA transcript resulted in the reduction of frataxin protein levels in the cell as a whole. In biochemical assays, the reduction or loss of frataxin protein yielded a phenotype mimicking FRDA in animal models and humans.

Figure 2:
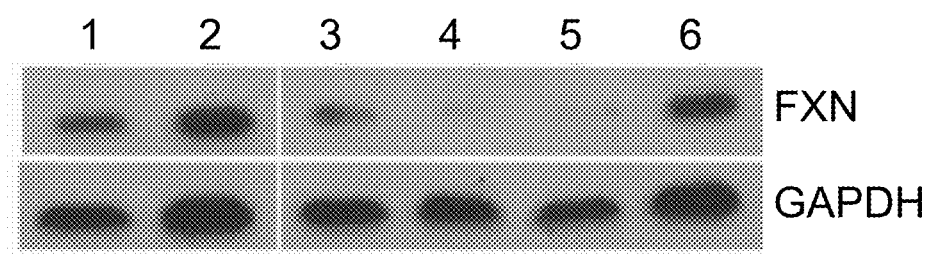
FIG. 2 is a Western blot showing the inducible FXN knockdown of FXN as discussed in Example 2.

C2C12 cells were grown in 96-well plates in the presence of hexdimethrine (8 µg/ml) to a confluence of 70%, and lentiviral particles were added. A multiplicity of infection (MOI) of 0.5, 1, and 5 were observed for efficacy. Media was changed 18 hours post infection. On Day 4, puromycin (1.6 µg/ml) was added to select for successful transduction. Surviving cells were seeded in new wells at single colony density under puromycin selection. After expansion, cell lines were evaluated for cell viability at different induction levels. Cells were evaluated at 15 days post-induction to allow for sufficient frataxin turnover, and the subsequent effects of the frataxin reduction to cascade throughout the pathway. Cell lines that were most robust in response to IPTG were initially assessed by a reduction in the cell expansion rate. The cell lines most affected, but still viable, were assayed via Western blot for reduced frataxin protein levels. FIG. 2 shows the Western bloting results for cell lines and controls. Each lane was coupled with a GAPDH loading control (shown directly below FXN lanes). Each lane reflects 25 µg of whole cell lysate, loaded sequentially as follows: Lane 1—C2C12 wt cells; Lane 2—C2C12 wt+IPTG; Lane 3—C2C12 shRNA cells-191+IPTG; Lane 4—C2C12 shRNA cells-176+IPTG; Lane 5—C2C12 shRNA cells-173+IPTG; Lane 6—C2C12 shRNA cells-scrabbled shRNA+IPTG.

Figure 3:
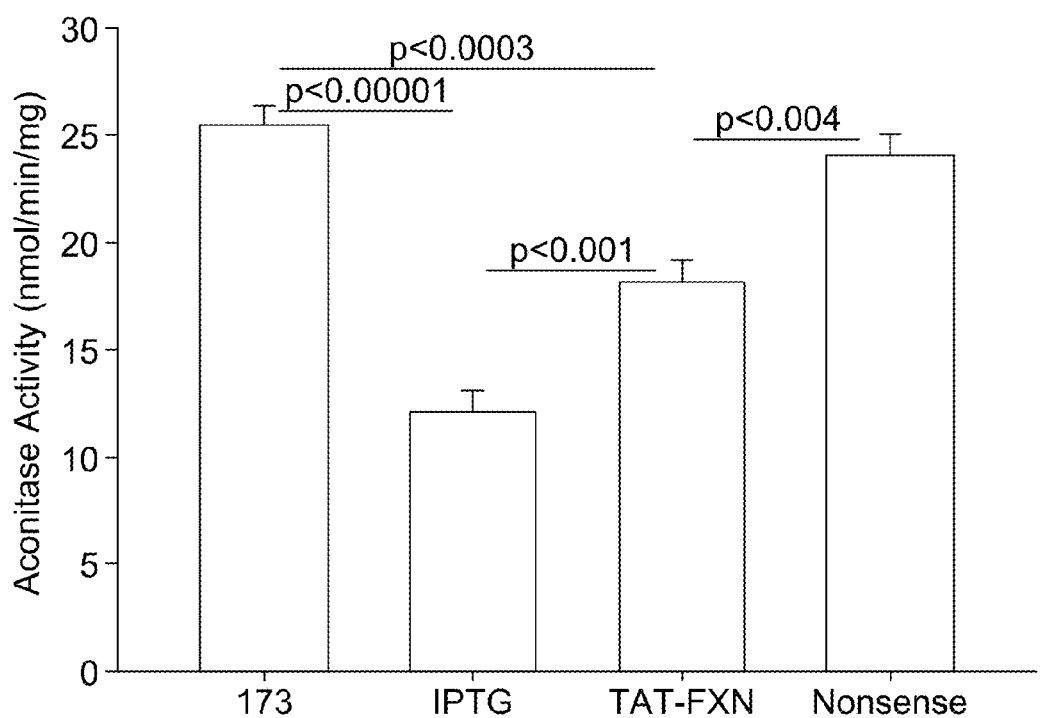
FIG. 3 is a graph depicting aconitase activity in the 173 cell line as discussed in Example 2.

Cell line 173 showed the greatest knockdown of frataxin and was assessed for aconitase activity using a commercially available kit (Cayman Chemicals, Ann Arbor, Mich.). Aconitase is an enzyme whose functionality is directly enabled by frataxin and is a sensitive marker of the loss of frataxin protein. The results of two separate experiments were pooled. As shown in FIG. 3, the aconitase activity of IPTG-induced 173 cells was decreased.

Example 3

In this Example, the efficacy of cell line 173 for use as a candidate therapeutic agent screening tool is described.

IPTG-induced 173 cells were treated with TAT-Frataxin. TAT-Frataxin rescues the animal model of FRDA. As shown in FIG. 3, TAT-Frataxin treatment of IPTG-induced 173 cells substantially and significantly improved aconitase activity.

Figure 4:
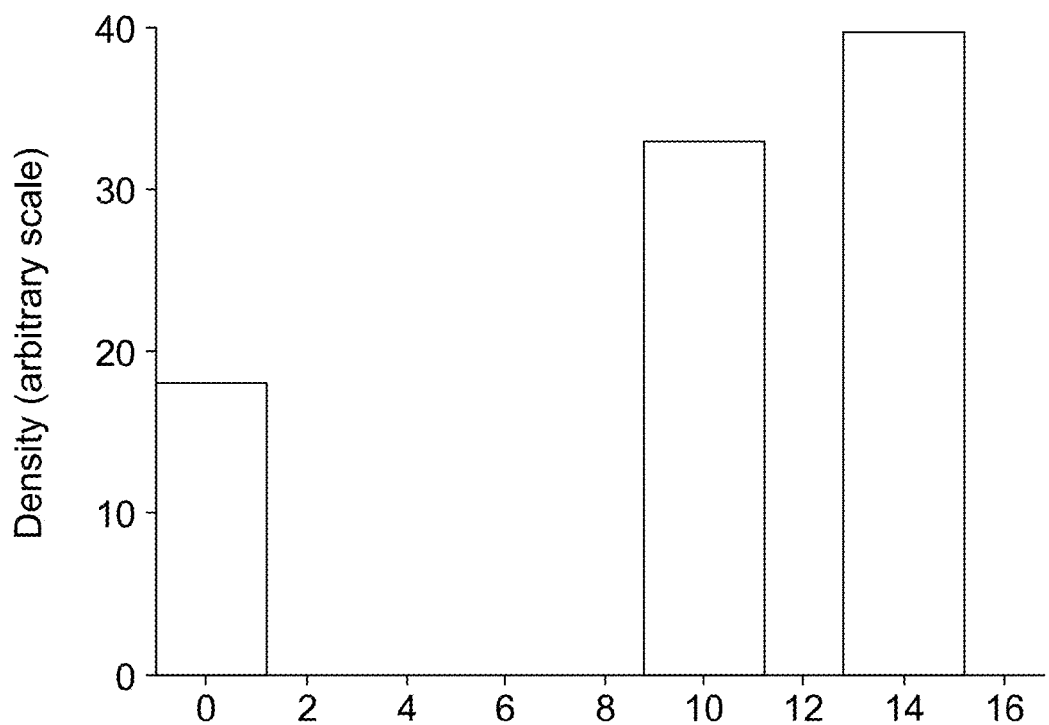
FIG. 4 is a graph depicting the progressive acetylation of proteins with the loss of FXN as discussed in Example 3.

The IPTG-induced 173 cells also report on protein acetylation in FRDA, which is a novel mitochondrial finding in FRDA (Wagner, et al, Human Molecular Genetics, 2012). 173 cells were induced with IPTG for 10 or 14 days. Whole cell homogenate was separated by SDS-PAGE and transferred to nitrocellulose for immunoblotting with an anti-acetyl antibody. Signal from anti-acetyl antibody was normalized to protein loading. As shown in FIG. 4, a substantial and progressive acetylation of proteins was observed with the loss of FXN.

Advantageously, the stable cell line of the present disclosure exhibits FRDA characteristics in an inducible fashion. Moreover, the expression vector construct expresses an shRNA molecule in a dose-responsive fashion. A particular advantage of the cell line of the present disclosure is that the titratable nature of this induced knockdown distinguishes this cell model from other cell culture models in which frataxin is either lost or not. The ability to control the knockout of frataxin through the titration of induction advantageously allows for the reduction of frataxin protein level over a wide range of concentrations. Additionally, the C2C12 myoblast cells transduced with the expression vector construct of the present disclosure grow rapidly and stably in the absence of induction, thus allowing for rapid expansion, frequent platings, and reproducible results. When induced, the degree of frataxin knockdown is titratable allowing for screening of candidate therapeutic agents and mechanistic studies. Further, the variability found in patient primary cells is eliminated allowing for consistent longitudinal comparisons of potential therapeutic agents.

In view of the above, it will be seen that the several advantages of the disclosure are achieved and other advantageous results attained. As various changes could be made in the above compositions and methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A recombinant nucleic acid construct for frataxin knockdown comprising a nucleic acid encoding an shRNA, wherein the shRNA comprises a sequence selected from the group consisting of SEQ ID NO: 1, SEQ ID NO: 2 and SEQ ID NO: 3, wherein the shRNA is operably linked to a heterologous expression control sequence.

2. The recombinant nucleic acid construct of claim 1 wherein the heterologous expression control sequence is selected from the group consisting of an inducible promoter and a constitutive promoter.

3. The recombinant nucleic acid construct of claim 2 wherein the inducible promoter is an isopropylthio-β-galactoside-inducible promoter.

4. An isolated transduced cell comprising an expression vector comprising a nucleic acid sequence encoding an shRNA, wherein the shRNA comprises a sequence selected from the group consisting of SEQ ID NO: 1, SEQ ID NO: 2 and SEQ ID NO: 3, and a heterologous expression control sequence.

5. The isolated transduced cell of claim 4 wherein the cell is a C2C12 myoblast cell.

6. The isolated transduced cell of claim 4 wherein the heterologous expression control sequence is selected from the group consisting of an inducible promoter and a constitutive promoter.

7. The isolated transduced cell of claim 6 wherein the inducible promoter is an isopropylthio-β-galactoside-inducible promoter.

8. The isolated transduced cell of claim 4 wherein the expression vector comprises a lentiviral construct.

9. A method of screening for a candidate therapeutic agent for treating Friedreich's Ataxia, the method comprising:
culturing an isolated C2C12 myoblast transduced cell comprising an expression vector comprising a nucleic acid sequence encoding an shRNA, wherein the shRNA comprises a sequence selected from the group consisting of SEQ ID NO: 1, SEQ ID NO: 2 and SEQ ID NO: 6, and a heterologous expression control sequence;
inducing the isolated transduced cell to express the shRNA, wherein the shRNA reduces frataxin mRNA transcripts;
contacting the isolated transduced cell with a candidate therapeutic agent; and
analyzing the isolated transduced cell contacted with the candidate therapeutic agent.

10. The method of claim 9 wherein the heterologous expression control sequence is selected from the group consisting of an inducible promoter and a constitutive promoter.

11. The method of claim 10 wherein the inducible promoter is an isopropylthio-β-galactoside-inducible promoter.

12. The method of claim 9 wherein the expression vector comprises a lentiviral construct.

13. The method of claim 9 wherein analyzing the isolated transduced cell contacted with the candidate therapeutic agent comprises analyzing frataxin protein level.

14. The method of claim 9 wherein analyzing the isolated transduced cell contacted with the candidate therapeutic agent comprises analyzing aconitase activity.

15. The method of claim 14 wherein the aconitase activity is increased.

16. The method of claim 9 wherein analyzing the isolated transduced cell contacted with the candidate therapeutic agent comprises analyzing protein acetylation.

17. The method of claim 16 wherein protein acetylation is increased.

18. The method of claim 9 wherein the candidate therapeutic agent is selected from the group consisting of small molecule drugs, peptides, lipids, protein drugs, protein conjugate drugs, enzymes, oligonucleotides, ribozymes and combinations thereof.

* * * * *